US008340379B2

(12) United States Patent
Razzaque et al.

(10) Patent No.: US 8,340,379 B2
(45) Date of Patent: Dec. 25, 2012

(54) SYSTEMS AND METHODS FOR DISPLAYING GUIDANCE DATA BASED ON UPDATED DEFORMABLE IMAGING DATA

(75) Inventors: Sharif Razzaque, Chapel Hill, NC (US); Andrei State, Chapel Hill, NC (US)

(73) Assignee: Inneroptic Technology, Inc., Hillsborough, NC (US)

( * ) Notice: Subject to any disclaimer, the term of this patent is extended or adjusted under 35 U.S.C. 154(b) by 754 days.

(21) Appl. No.: 12/399,899

(22) Filed: Mar. 6, 2009

(65) Prior Publication Data
US 2009/0226069 A1   Sep. 10, 2009

Related U.S. Application Data

(60) Provisional application No. 61/068,469, filed on Mar. 7, 2008.

(51) Int. Cl.
*G06K 9/00* (2006.01)
(52) U.S. Cl. ........ 382/128; 382/131; 600/424; 600/426; 623/902
(58) Field of Classification Search .................. 382/128, 382/131, 132; 606/41, 28; 623/902, 903, 623/904, 905, 906, 907, 22.15; 600/424, 600/426, 407
See application file for complete search history.

(56) References Cited

U.S. PATENT DOCUMENTS

| RE30,397 E | 9/1980 | King |
| 4,294,544 A | 10/1981 | Altschuler et al. |
| 4,862,873 A | 9/1989 | Yajima et al. |
| 4,884,219 A | 11/1989 | Waldren |
| 5,109,276 A | 4/1992 | Nudelman et al. |
| 5,193,120 A | 3/1993 | Gamache et al. |
| 5,249,581 A | 10/1993 | Horbal et al. |

(Continued)

FOREIGN PATENT DOCUMENTS
CN    1636520    7/2005
(Continued)

OTHER PUBLICATIONS

Stephen R. Aylward, Julien Jomier, Sue Weeks and Elizabeth Bullitt, *Registration and Analysis of Vascular Images*, International Journal of Computer Vision 55(2/3), 123-138, 2003.

(Continued)

*Primary Examiner* — Francis M Legasse, Jr.
(74) *Attorney, Agent, or Firm* — Knobbe Martens Olson & Bear LLP

(57) ABSTRACT

Presented herein are methods, systems, and computer-readable medium for presenting imaging data related to an anatomical site. These include obtaining a first set of imaging data related to the anatomical site and tracking units at the anatomical site and, thereafter, optionally, obtaining a second set of imaging data related to the anatomical site. A deformed version of the first set of imaging data is then determined based on the relative arrangements of one or more of the tracking units at the time when the first set of imaging data is obtained and when the second set of imaging data is obtained. Then the relative emplacements of the second set of imaging data set and of the deformed version of the first set of imaging data set are determined and used, along with the second set of imaging data set and the deformed version of the first set of imaging data, as a basis for displaying image guidance data.

17 Claims, 8 Drawing Sheets

U.S. PATENT DOCUMENTS

| | | |
|---|---|---|
| 5,261,404 A | 11/1993 | Mick et al. |
| 5,307,153 A | 4/1994 | Maruyama et al. |
| 5,323,002 A | 6/1994 | Sampsell et al. |
| 5,371,543 A | 12/1994 | Anderson |
| 5,383,454 A | 1/1995 | Bucholz |
| 5,446,798 A | 8/1995 | Morita et al. |
| 5,452,024 A | 9/1995 | Sampsell |
| 5,457,493 A | 10/1995 | Leddy et al. |
| 5,488,431 A | 1/1996 | Gove et al. |
| 5,489,952 A | 2/1996 | Gove et al. |
| 5,491,510 A | 2/1996 | Gove |
| 5,517,990 A | 5/1996 | Kalfas et al. |
| 5,526,051 A | 6/1996 | Gove et al. |
| 5,532,997 A | 7/1996 | Pauli |
| 5,541,723 A | 7/1996 | Tanaka |
| 5,570,135 A | 10/1996 | Gove et al. |
| 5,579,026 A | 11/1996 | Tabata |
| 5,588,948 A | 12/1996 | Takahashi et al. |
| 5,608,468 A | 3/1997 | Gove et al. |
| 5,611,353 A | 3/1997 | Dance et al. |
| 5,612,753 A | 3/1997 | Poradish et al. |
| 5,625,408 A | 4/1997 | Matsugu et al. |
| 5,629,794 A | 5/1997 | Magel et al. |
| 5,630,027 A | 5/1997 | Venkateswar et al. |
| 5,699,444 A | 12/1997 | Palm |
| 5,726,670 A | 3/1998 | Tabata et al. |
| 5,766,135 A | 6/1998 | Terwilliger |
| 5,784,098 A | 7/1998 | Shoji et al. |
| 5,807,395 A | 9/1998 | Mulier et al. |
| 5,820,554 A | 10/1998 | Davis et al. |
| 5,870,136 A | 2/1999 | Fuchs et al. |
| 5,891,034 A | 4/1999 | Bucholz |
| 6,019,724 A | 2/2000 | Gronningsaeter et al. |
| 6,064,749 A | 5/2000 | Hirota et al. |
| 6,095,982 A | 8/2000 | Richards-Kortum et al. |
| 6,108,130 A | 8/2000 | Raj |
| 6,122,541 A | 9/2000 | Cosman et al. |
| 6,167,296 A | 12/2000 | Shahidi |
| 6,216,029 B1 | 4/2001 | Paltieli |
| 6,246,898 B1 | 6/2001 | Vesely et al. |
| 6,261,234 B1 | 7/2001 | Lin |
| 6,341,016 B1 | 1/2002 | Malione |
| 6,348,058 B1 | 2/2002 | Melkent |
| 6,385,475 B1 | 5/2002 | Cinquin et al. |
| 6,442,417 B1 | 8/2002 | Shahidi et al. |
| 6,456,868 B2 | 9/2002 | Saito et al. |
| 6,470,207 B1 | 10/2002 | Simon et al. |
| 6,477,400 B1 | 11/2002 | Marrick |
| 6,478,793 B1 | 11/2002 | Cosman et al. |
| 6,503,195 B1 | 1/2003 | Keller et al. |
| 6,511,418 B2 | 1/2003 | Shahidi et al. |
| 6,518,939 B1 | 2/2003 | Kikuchi |
| 6,527,443 B1 | 3/2003 | Vilsmeier et al. |
| 6,529,758 B2 | 3/2003 | Shahidi |
| 6,545,706 B1 | 4/2003 | Edwards et al. |
| 6,546,279 B1 | 4/2003 | Bova et al. |
| 6,551,325 B2 | 4/2003 | Neubauer et al. |
| 6,570,566 B1 | 5/2003 | Yoshigahara |
| 6,587,711 B1 | 7/2003 | Alfano et al. |
| 6,591,130 B2 | 7/2003 | Shahidi |
| 6,594,517 B1 | 7/2003 | Nevo |
| 6,597,818 B2 | 7/2003 | Kumar et al. |
| 6,626,832 B1 | 9/2003 | Paltieli et al. |
| 6,689,067 B2 | 2/2004 | Sauer et al. |
| 6,711,429 B1 | 3/2004 | Gilboa et al. |
| 6,725,082 B2 | 4/2004 | Sati et al. |
| 6,733,458 B1 | 5/2004 | Steins et al. |
| 6,764,449 B2 | 7/2004 | Lee et al. |
| 6,766,184 B2 | 7/2004 | Utzinger et al. |
| 6,768,496 B2 | 7/2004 | Bieger et al. |
| 6,775,404 B1 | 8/2004 | Pagoulatos et al. |
| 6,782,287 B2 | 8/2004 | Grzeszczuk et al. |
| 6,783,524 B2 | 8/2004 | Anderson et al. |
| 6,827,723 B2 | 12/2004 | Carson |
| 6,873,867 B2 | 3/2005 | Vilsmeier |
| 6,881,214 B2 | 4/2005 | Cosman et al. |
| 6,895,268 B1 | 5/2005 | Rahn et al. |
| 6,915,150 B2 | 7/2005 | Cinquin et al. |
| 6,917,827 B2 | 7/2005 | Kienzle, III |
| 6,923,817 B2 | 8/2005 | Carson et al. |
| 6,947,783 B2 | 9/2005 | Immerz |
| 6,968,224 B2 | 11/2005 | Kessman et al. |
| 6,978,167 B2 | 12/2005 | Dekel et al. |
| 7,008,373 B2 | 3/2006 | Stoianovici et al. |
| 7,033,360 B2 | 4/2006 | Cinquin et al. |
| 7,072,707 B2 | 7/2006 | Galloway, Jr. et al. |
| 7,110,013 B2 | 9/2006 | Ebersole et al. |
| 7,209,776 B2 | 4/2007 | Leitner |
| 7,248,232 B1 | 7/2007 | Yamazaki et al. |
| 7,331,932 B2 | 2/2008 | Leitner |
| 7,385,708 B2 | 6/2008 | Ackerman |
| 7,392,076 B2 | 6/2008 | Moctezuma de La Barrera |
| 7,398,116 B2 | 7/2008 | Edwards |
| 7,480,533 B2 | 1/2009 | Cosman et al. |
| 7,505,809 B2 | 3/2009 | Strommer et al. |
| 7,728,868 B2 | 6/2010 | Razzaque et al. |
| 7,833,221 B2 | 11/2010 | Voegele et al. |
| 7,876,942 B2 | 1/2011 | Gilboa |
| 7,920,909 B2 | 4/2011 | Lyon et al. |
| 7,962,193 B2 | 6/2011 | Edwards et al. |
| 8,041,413 B2 | 10/2011 | Barbagli et al. |
| 8,052,636 B2 | 11/2011 | Moll et al. |
| 8,073,528 B2 | 12/2011 | Zhao et al. |
| 2001/0007919 A1 | 7/2001 | Shahidi |
| 2001/0016804 A1 | 8/2001 | Cunningham et al. |
| 2001/0045979 A1 | 11/2001 | Matsumoto et al. |
| 2002/0010384 A1 | 1/2002 | Shahidi et al. |
| 2002/0049375 A1 | 4/2002 | Strommer et al. |
| 2002/0077540 A1 | 6/2002 | Kienzle, III |
| 2002/0077543 A1 | 6/2002 | Grzeszczuk et al. |
| 2002/0135673 A1 | 9/2002 | Favalora et al. |
| 2002/0138008 A1 | 9/2002 | Tsujita et al. |
| 2002/0140814 A1 | 10/2002 | Cohen-Solal et al. |
| 2002/0156375 A1* | 10/2002 | Kessman et al. .............. 600/439 |
| 2002/0198451 A1 | 12/2002 | Carson |
| 2003/0040743 A1 | 2/2003 | Cosman et al. |
| 2003/0073901 A1 | 4/2003 | Simon et al. |
| 2003/0164172 A1 | 9/2003 | Chumas et al. |
| 2003/0231789 A1 | 12/2003 | Willis et al. |
| 2004/0034313 A1 | 2/2004 | Leitner |
| 2004/0078036 A1 | 4/2004 | Keidar |
| 2004/0095507 A1 | 5/2004 | Bishop et al. |
| 2004/0147920 A1 | 7/2004 | Keidar |
| 2004/0181144 A1 | 9/2004 | Cinquin et al. |
| 2004/0238732 A1 | 12/2004 | State et al. |
| 2004/0243148 A1 | 12/2004 | Wasielewski |
| 2004/0254454 A1 | 12/2004 | Kockro |
| 2005/0085717 A1 | 4/2005 | Shahidi |
| 2005/0085718 A1 | 4/2005 | Shahidi |
| 2005/0090742 A1 | 4/2005 | Mine et al. |
| 2005/0111733 A1 | 5/2005 | Fors et al. |
| 2005/0159641 A1 | 7/2005 | Kanai |
| 2005/0182316 A1 | 8/2005 | Burdette et al. |
| 2005/0192564 A1 | 9/2005 | Cosman et al. |
| 2005/0219552 A1 | 10/2005 | Ackerman et al. |
| 2005/0222574 A1 | 10/2005 | Giordano et al. |
| 2005/0251148 A1 | 11/2005 | Friedrich et al. |
| 2006/0004275 A1 | 1/2006 | Vija et al. |
| 2006/0036162 A1 | 2/2006 | Shahidi et al. |
| 2006/0052792 A1 | 3/2006 | Boettiger et al. |
| 2006/0100505 A1 | 5/2006 | Viswanathan |
| 2006/0122495 A1 | 6/2006 | Cosman et al. |
| 2006/0184040 A1 | 8/2006 | Keller et al. |
| 2006/0193504 A1 | 8/2006 | Salgo et al. |
| 2006/0229594 A1 | 10/2006 | Francischelli et al. |
| 2006/0235290 A1 | 10/2006 | Gabriel et al. |
| 2006/0235538 A1 | 10/2006 | Rochetin et al. |
| 2006/0253030 A1 | 11/2006 | Altmann et al. |
| 2006/0253032 A1 | 11/2006 | Altmann et al. |
| 2006/0271056 A1 | 11/2006 | Terrill-Grisoni et al. |
| 2006/0282023 A1 | 12/2006 | Leitner |
| 2006/0293643 A1 | 12/2006 | Wallace et al. |
| 2007/0032906 A1 | 2/2007 | Sutherland et al. |
| 2007/0167699 A1 | 7/2007 | Lathuiliere et al. |
| 2007/0167701 A1 | 7/2007 | Sherman |
| 2007/0167801 A1 | 7/2007 | Webler et al. |
| 2007/0225553 A1 | 9/2007 | Shahidi |

| | | |
|---|---|---|
| 2007/0239281 A1 | 10/2007 | Gotte et al. |
| 2007/0244488 A1 | 10/2007 | Metzger et al. |
| 2007/0270718 A1 | 11/2007 | Rochetin et al. |
| 2007/0276234 A1 | 11/2007 | Shahidi |
| 2008/0004516 A1 | 1/2008 | DiSilvestro et al. |
| 2008/0030578 A1 | 2/2008 | Razzaque et al. |
| 2008/0051910 A1 | 2/2008 | Kammerzell et al. |
| 2008/0091106 A1 | 4/2008 | Kim et al. |
| 2008/0161824 A1 | 7/2008 | McMillen |
| 2008/0200794 A1 | 8/2008 | Teichman et al. |
| 2008/0208205 A1 | 8/2008 | Murphy et al. |
| 2008/0214932 A1 | 9/2008 | Mollard et al. |
| 2008/0232679 A1 | 9/2008 | Hahn et al. |
| 2008/0287805 A1 | 11/2008 | Li |
| 2009/0226069 A1 | 9/2009 | Razzaque et al. |
| 2009/0312629 A1 | 12/2009 | Razzaque et al. |
| 2010/0045783 A1 | 2/2010 | State et al. |
| 2010/0198045 A1 | 8/2010 | Razzaque et al. |
| 2010/0268067 A1 | 10/2010 | Razzaque et al. |
| 2011/0043612 A1 | 2/2011 | Keller et al. |
| 2011/0057930 A1 | 3/2011 | Keller |
| 2011/0082351 A1 | 4/2011 | Razzaque et al. |
| 2011/0130641 A1 | 6/2011 | Razzaque et al. |
| 2011/0137156 A1 | 6/2011 | Razzaque et al. |
| 2011/0251483 A1 | 10/2011 | Razzaque et al. |
| 2012/0101370 A1 | 4/2012 | Razzaque et al. |
| 2012/0108955 A1 | 5/2012 | Razzaque et al. |

FOREIGN PATENT DOCUMENTS

| | | |
|---|---|---|
| CN | 100381108 | 4/2008 |
| EP | 1955284 | 8/2008 |
| JP | 2005-058584 | 3/2005 |
| JP | 2005-323669 | 11/2005 |
| JP | 2009-517177 | 4/2009 |
| WO | PCT/US2003/017987 | 12/2003 |
| WO | WO 2007-067323 A2 | 6/2007 |
| WO | WO 2007-067323 A3 | 9/2007 |
| WO | WO 2008017051 A2 * | 2/2008 |
| WO | PCT/2009/032028 | 1/2009 |
| WO | WO 2009-094646 | 7/2009 |
| WO | WO 2010-096419 | 8/2010 |

OTHER PUBLICATIONS

Stephen R. Aylward, Julien Momier, Jean-Philippe Guyon, Susan Weeks, *Intra-Operative 3D Ultrasound Augmentation*, Proceedings of the IEEE International Symposium on Biomedical Imaging, Washington, Jul. 2002.

Armond L. Levy, Timothy J. Schaewe, Michael I. Miller, Kurt R. Smith, Abed M. Hammoud, Jaimie M. Henderson, Sarang Joshi, Kevin E. Mark, Christophewr D. Sturm, Leslie L. McDurmont, Jr. and Richard D. Bucholz, *An Internet-Connected, Patient Specific, Deformable Brain Atlas Integrated into a Surgical Navigation System*, Journal of Digital Imaging, vol. 10, No. 3. Suppl. 1 (Aug.) 1997: pp. 231-237.

Alan J. Herline, M.D., Jeannette L. Herring, Ph.D., James D. Stefansic, M.S., William C. Chapman, M.D., Robert L. Galloway, Jr., Ph.D., Benoit M. Dawant, Ph.D. *Surface Registration for Use in Interactive, Image-Guided Liver Surgery*, Computer Aided Surgery 5:11-17 (2000).

Marseea H. Howard, M.D., Rendon C. Nelson, M.D., Erik K. Paulson, M.D., Mark A. Kliewer, M.D., Douglas H. Sheafor, M.D., *An Electronic Device for Needle Placement during Sonographically Guided Percutaneous intervention*, Radiology 2001; 218:905-911.

Stephen R. Aylward, Sue Weeks, and Elizabeth Bullitt *Analysis of the Parameter Space of a Metric for Registering 3D Vascular Images*, in W. Niessen and M. Viergever (Eds.): MICCAI 2001, LNCS 2208, pp. 932-939, 2001.

Che Yinghui, Wang Jing, Liang Ziaohui *Real-Time Deformation Using Modal Analysis on Graphics Hardware*, Graphite 2006, Kuala Lumpur, Malaysia, Nov. 29-Dec. 2, 2006.

"3D Laparoscope Technology," http://www.inneroptic.com/tech_3DL.htm, copyright 2007 InnerOptic Technology, Inc. printed Sep. 19, 2007, 2 pages.

"Cancer Facts & Figures 2004," www.cancer.org/downloads/STT/CAFF_finalPWSecured.pdf, copyright 2004 American Cancer Society, Inc., printed Sep. 19, 2007, 60 pages.

"David Laserscanner <-Latest News <- Institute for Robotics and Process Control <- Te . . . ," http://www/rob.cs.tu-bs.de/en/news/david, printed Sep. 19, 2007, 1 page.

"Laser scanned 3d model Final" video, still image of video attached, http://www.youtube.com/watch?v+DaLglgmoUf8, copyright 2007 YouTube, LLC, printed Sep. 19, 2007, 2 pages.

"Mike robbins—Computer Vision Research—Stereo Depth Perception," http://www.compumike.com/vision/stereodepth. php, copyright 2007 Michael F. Robbins, printed Sep. 19, 2007, 3 pages.

"Olympus Endoscopic Ultrasound System," www.olympusamerica.com/msg_section/download_brochures/135_b_gfum130.pdf, printed Sep. 20, 2007, 20 pages.

"Point Grey Research Inc.—Imaging Products—Triclops SDK Samples," http://www.ptgrey.com/products/triclopsSDK/samples.asp, copyright 2007 Point Grey Research Inc., printed Sep. 19, 2007, 1 page.

"RUE: Registered Ultrasound-Endoscope," copyright 2007 InnerOptic Technology, Inc., 2 pages.

Advertisement, "Inspeck 3DC 3D Capturor," Inspeck 3DC 3D Capturor (www.inspeck.com), 1998.

Advertisement, "Virtual 3D High Speed Non-Contact Surface Perception," Virtual 3-D Technologies Corporation (www.virtual3dtech.com)., Dec. 21, 1998.

Advertisements, "Virtuoso," Visual Interface, Inc. (www.visint.com), Dec. 21, 1998.

Akka, "Automatic Software Control of Display Parameters for Stereoscopic Graphics Images," SPIE vol. 1669: Stereoscopic Displays and Applications III, pp. 31-38 (1992).

Ali et al., "Near Infrared Spectroscopy and Imaging to Probe Differences in Water Content in Normal and Cancer Human Prostate Tissues," Technology in Cancer Research & Treatment; Oct. 2004; 3(5):491-497; Adenine Press.

Amir Lass, "Assessment of Ovarian Reserve," Human Reproduction, 2004, vol. 19(3), pp. 467-469, available from http://humrep.oxfordjournals.orgcgi/reprint/119/3/467, printed Sep. 20, 2007, 3 pages.

Andrei State et al., "Case Study: Observing a Volume Rendered Fetus within a Pregnant Patient," Proceedings of IEEE Visualization 1994, pp. 364-368, available from www.cs.unc.edu/~fuchs/publications/cs-ObservVolRendFetus94.pdf, printed Sep. 20, 2007, 5 pages.

Andrei State et al., "Interactive Volume Visualization on a Heterogenous Message-Passing Multicomputer," Proceedings of 1995 Symposium on Interactive 3D Graphics, 1995, pp. 69-74, 208, available from www.cs.unc.edu/~andrei/pubs/1995_13D_vol2_Mac.pdf, printed Sep. 20, 2007.

Andrei State et al., "Simulation-Based Design and Rapid Prototyping of a Parallax-Free, Orthoscopic Video See-Through Head-Mounted Display," Proceedings of International Symposium on Mixed and Augmented Reality (ISMAR) 2005, available from www.cs.unc.edu/~ andrei/pubs/2005_ISMAR_VSTHMD_design.pdf, printed Sep. 20, 2007, 4 pages.

Andrei State et al., "Stereo Imagery from the UNC Augmented Reality System for Breast Biopsy Guidance" Proc. Medicine Meets Virtual Reality (MMVR) 2003 (Newport Beach, CA, Jan. 22-25, 2003).

Andrei State et al., "Superior Augmented Reality Registration by Integrating Landmark Tracking and Magnetic Tracking," ACM SIGGRAPH Computer Graphics, Proceedings of SIGGRAPH 1996, pp. 429-438, available from www.cs.princeton.edu/courses/archive/fall01/cs597d/papers/state96.pdf, printed Sep. 20, 20007, 10 pages.

Andrei State et al., "Technologies for Augmented Reality Systems: Realizing Ultrasound-Guided Needle Biopsies," Computer Graphics, Proceedings of SIGGRAPH 1996, pp. 429-438, available from www.cs.princeton.edu/courses/archive/fall01/cs597d/papers/state96.pdf, printed Sep. 20, 2007.

Andrei State. "Exact Eye Contact with Virtual Humans." Proc. IEEE International Workshop on Human Computer Interaction 2007 (Rio de Janeiro, Brazil, Oct. 20, 2007), pp. 138-145.

Aylward et al., Analysis of the Parameter Space of a Metric for Registering 3D Vascular Images, in W. Niessen and M. Viergever (Eds.): MICCAI 2001, LNCS 2208, pp. 932-939, 2001.

Aylward et al., Intra-Operative 3D Ultrasound Augmentation, Proceedings of the IEEE International Symposium on Biomedical Imaging, Washington, Jul. 2002.

Aylward et al., Registration and Analysis of Vascular Images, International Journal of Computer Vision 55(2/3), 123-138, 2003.

Azuma, "A Survey of Augmented Reality," Presence: Teleoperators and Virtual Environments 6, 4:1-48 (Aug. 1997).

Azuma, R., Bishop, G.; Improving Static and Dynamic Registration in an Optical See-Through HMO; Proceedings of SIGGRAPH '94, Computer Graphics, Annual Conference Series, 1994, 197-204 (1994).

Benavides et al., "Multispectral digital colposcopy for in vivo detection of cervical cancer," Optics Express; May 19, 2003; 11(1 0) Optical Society of America; USA.

Beraldin, J.A. et al., "Optimized Position Sensors for Flying-Spot Active Triangulation Systems, " Proceedings of the Fourth International Conference on a 3-D Digital Imaging and Modeling (3DIM), Banff, Alberta, Canada, Oct. 6-10, 2003, pp. 334-341, NRC 47083, copyright 2003 National Research Council of Canada, http://iit-iti.nrc-cnrc.gc.ca/iit-publications-iti/docs/NRC-47083.Pdf, printed Sep. 19, 2007, 9 pages.

Billinghurst, M., Henrysson, A.; Research Directions in Handheld AR; Int. J. of Virtual Reality 5(2),51-58 (2006).

Blais, F., "Review of 20 Years of Range Sensor Development," Journal of Electronic Imaging, 13(1): 231-240, Jan. 2004, NRC 46531, copyright 2004 National Research Council of Canada, http://iit-iti.nrc-cnrc.gc.ca/iit-publications-iti/docs/NRC-46531.pdf, printed Sep. 19, 2007, 14 pages.

Brian W. Progue et al., "Analysis of acetic acid-induced whitening of high-grade squamous intraepitheliallesions," Journal of Biomedical Optics; Oct. 2001; 6(4):397-403.

Buxton et al.; "Colposcopically directed punch biopsy: a potentially misleading investigation," British Journal of Obstetrics and Gynecology; Dec. 1991; 98:1273-1276.

Cancer Prevention & Early Detection Facts & Figures 2004; National Center for Tobacco-Free Kids; 2004; American Cancer Society; USA.

Cantor et al., "Cost-Effectiveness Analysis of Diagnosis and Management of Cervical Squamous Intraepithelial Lesions," Diagnostic Strategies for SILs; Feb. 1998; 91(2):270-277.

Catalano et al. "Multiphase helical CT findings after percutaneous ablation procedures for hepatocellular carcinoma." Abdom. Imaging, 25(6),2000, pp. 607-614.

Chiriboga et al., "Infrared Spectroscopy of Human Tissue. IV. Detection of Dysplastic and Neoplastic Changes of Human Cervical Tissue Via Infrared Microscopy," Cellular and Molecular Biology; 1998; 44(1): 219-229.

Depiero et al., "3-D Computer Vision Using Structured Light: Design, Calibration and Implementation Issues," The University of Tennessee, pp. 1-46, (1996).

Drascic et al., "Perceptual Issues in Augmented Reality," SPIE vol. 2653: Stereoscopic Displays and Virtual Reality Systems III, pp. 123-134 (Feb. 1996).

E. David Crawford et al., "Computer Modeling of Prostate Biopsy: Tumor Size and Location—Not Clinical Significance—Determine Cancer Detection," Journal of Urology, Apr. 1998, vol. 159(4), pp. 1260-1264, 5 pages.

Fahey et al., "Meta-analysis of Pap Test Accuracy; American Journal of Epidemiology," 1995 141(7):680-689; The John Hopkins University School of Hygiene and Public Health; USA.

Foxlin et al., An Inertial Head-Orientation Tracker with Automatic Drift Compensation for Use with HMD's, in Virtual Reality Software & Technology, Proceedings of the VRST Conference, pp. 159-173, Singapore, Aug. 23-26, 1994.

Fronheiser et al., Real-Time 3D Color Doppler for Guidance of Vibrating Interventional Devices, IEEE Ultrasonics Symposium, pp. 149-152 (2004).

Fuhrmann, A., Splechtna, R., Pikryl, J.; Comprehensive calibration and registration procedures for augmented reality; Proc. Eurographics Workshop on Virtual Environments 2001,219-228.

G.D. Dodd et al. "Minimally invasive treatment of malignant hepatic tumors: at the threshold of a major breakthrough." Radiographies 20(1),2000, pp. 9-27.

Georgakoudi et al., "Trimodal spectroscopy for the detection and characterization of cervical precancers in vivo," American Journal of Obstetrics and Gynecology; Mar. 2002; 186(3):374-382; USA.

Henry Fuchs et al., "Augmented Reality Visualization for Laparoscopic Surgery," Proceedings of Medical Image Computing and Computer-Assisted Intervention (MICCAI) 1998, pp. 934-943, available from www.cs.unc.edu/~fuchs/publications /AugRealVis$_{13}$ LaparoSurg98.pdf, printed Sep. 20, 2007, 10 pages.

Herline et al., Surface Registration for Use in Interactive, Image-Guided Liver Surgery, Computer Aided Surgery 5:11-17 (2000).

Holloway, R.; Registration Error Analysis for Augmented Reality; Presence: Teleoperators and Virtual Environments 6(4), 413-432 (1997).

Hornung et al., "Quantitative near-infrared spectroscopy of cervical dysplasia in vivo," Human Reproduction; 1999; 14(11):2908-2916; European Society of Human Reproduction and Embryology.

Jean-Yves Bouguet, "Camera Calibration Toolbox for Matlab," www.vision.caltech.edu/bouguetj/calib_doc, printed Sep. 20, 2007, 5 pages.

Kanbara et al., "A Stereoscopic Video See-through Augmented Reality System Based on Real-time Vision-Based Registration," Nara Institute of Science and Technology, pp. 1-8 (2000).

Lee et al., "Modeling Real Objects Using Video See-Through Augmented Reality," Presence, 11(2):144-157 (Apr. 2002).

Leven et al., DaVinci Canvas: A Telerobotic Surgical System with Integrated, Robot-Assisted, Laparoscopic Ultrasound Capability, in J. Duncan and G. Gerig (Eds.): MICCAI 2005, LNCS 3749, pp. 811-818, 2005.

Levy et al., An Internet-Connected, Patient Specific, Deformable Brain Atlas Integrated into a Surgical Navigation System, Journal of Digital Imaging, vol. 10, No. 3. Suppl. 1 Aug. 1997: pp. 231-237.

Marco C. Jacobs et al., "Managing Latency in Complex Augmented Reality Systems," ACM SIGGRAPH Proceedings of the Symposium of Interactive 3D Graphics 1997, pp. 49-54, available from www.cs.unc.edu/~us/Latency//ManagingRelativeLatency.html, printed Sep. 20, 2007, 12 pages.

Mark A. Livingston et al., "Magnetic Tracker Calibration for Improved Augmented Reality Registration," Presence: Teleoperators and Virtual Environments, 1997, vol. 6(5), pp. 532-546, available from www.cs.unc.edu/~andrei/pubs/1997_Presence_calibr.pdf, printed Sep. 20, 2007, 14 pages.

Matsunaga et al., "The Effect of the Ratio Difference of Overlapped Areas of Stereoscopic Images on each Eye in a Teleoperalion," Stereoscopic Displays and Virtual Reality Systems VII, Proceedings of SPIE, 3957:236-243 (2000).

Michael Bajura et al., "Merging Virtual Objects with the Real World: Seeing Ultrasound Imagery within the Patient," Computer Graphics, Proceedings of SIGGRAPH 1992, vol. 26(2), pp. 203-210, available from www.cs.unc.edu/~fuchs/publications/MergVirtObjs92.pdf, printed Sep. 20, 2007, 8 pages.

Michael Deering. "High Resolution Virtual Reality." Proceedings of SIGGRAPH '92, Computer Graphics, 26(2), 1992, pp. 195-202.

Michael Meehan et al., "Effect of Latency on Presence in Stressful Virtual Environment," Proceedings of IEEE Virtual Reality 2003, pp. 141-148, available from http://www.cs.unc.edu/~eve/pubs.html, printed Sep. 20, 2007, 9 pages.

Michael Rosenthal et al., "Augmented Reality Guidance for Needle Biopsies: An Initial Randomized, Controlled Trial in Phantoms," Proceedings of Medical Image Analysis, Sep. 2002, vol. 6(3), pp. 313-320, available from www.cs.unc.edu/~fuchs/publications/AugRealGuida_NeedleBiop02.pdf, printed Sep. 20, 2007, 8 pages.

Michael Rosenthal, et al. "Augmented Reality Guidance for Needle Biopsies: A Randomized, Controlled Trial in Phantoms," Proceedings of MICCAI 2001, eds. W. Niessen and M. Viergever, Lecture Notes in Computer Science, 2001, vol. 2208, pp. 240-248, available from www.cs.unc.edu/~us/AugmentedRealityAssistance.pdf, printed Sep. 20, 2007, 9 pages.

Milgram et al., "Adaptation Effects in Stereo due to Online Changes in Camera Configuration," SPIE vol. 1669-13, Stereoscopic Displays and Applications III, pp. 1-12 (1992).

Mitchell et al., "Colposcopy for the Diagnosis of Squamous Intraepithelial lesions: A metaanalysis," Obstetrics and Gynecology; Apr. 1998; 91(4):626-631.

Nakamoto et al., 3D Ultrasound System Using a Magneto-optic Hybrid Tracker for Augmented Reality Visualization in Laparoscopic Liver Surgery, in T. Dohi and R. Kikinis (Eds.): MICCAI 2002, LNCS 2489, pp. 148-155, 2002.

Nordstrom et al., "Identification of Cervical Intraepithelial Neoplasia (CIN) Using UV-Excited Fluorescence and Diffuse-Reflectance Tissue Spectroscopy," Lasers in Surgery and Medicine; 2001; 29; pp. 118-127; Wiley-Liss, Inc.

Ohbuchi et al. "An Incremental Volume Rendering Algorithm for Interactive 3D Ultrasound Imaging", UNC-CH Computer Science Technical Report TR91-003, (1991).

Ohbuchi et al., "Incremental Volume Reconstruction and Rendering for 3D Ultrasound Imaging," Visualization in Biomedical Computing, SPIE Proceedings, pp. 312-323, (Oct. 13, 1992).

Ohbuchi, "Incremental Acquisition and Visualization of 3D Ultrasound Images," Ph.D. Dissertation, UNC-CH Computer Science Technical Report TR95-023, (1993).

Paul A. Viola, Alignment by Maximization of Mutual Information, Ph.D. Dissertation, MIT-Artificial Intelligence Laboratory Technical Report No. 1548 (Jun. 1995).

PCT, The International Search Report of the International Searching Authority, mailed Sep. 9, 2009, for case PCT/US2009/032028.

PCT. The Written Opinion of the International Searching Authority, mailed Sep. 9, 2009, for case PCT/US2009/032028.

Raij, A.B., Johnsen, K., Dickerson, RF., Lok, B.C., Cohen, M.S., Duerson, M., Pauly, RR, Stevens, A.D., Wagner, P., Lind, D.S.; Comparing Interpersonal Interactions with a Virtual Human to Those with a Real Human; IEEE Transactions on Visualization and Computer Graphics 13(3), 443-457 (2007).

Robinett et al., "A Computational Model for the Stereoscopic Optics of a Head-Mounted Display," SPIE vol. 1457, Stereoscopic Displays and Applications II, pp. 140-160 (1991).

Rolland et al., "Towards Quantifying Depth and Size Perception in 3D Virtual Environments," Presence: Teleoperators and Virtual Environments 4, 1:1-21 (1995).

Rolland et al., Towards Quantifying Depth and Size Perception in Virtual Environments, Presence: Teleoperators and Virtual Environments, Winter 1995, vol. 4, Issue 1, pp. 24-49.

Takagi et al., "Development of a Stereo Video See-through HMD for AR Systems," IEEE, pp. 68-77 (2000).

Ultraguide 1000 System, Ultraguide, www.ultraguideinc.com, 1998.

van Staveren et al., "Light Scattering in Intralipid-10% in the wavelength range of 400-1100 nm," Applied Optics; Nov. 1991; 30(31):4507-4514.

Viola et al., "Alignment by Maximization of Mutual Information," International Journal of Computer Vision, vol. 24, No. 2, pp. 1-29 (1997).

Ware et al., "Dynamic Adjustment of Stereo Display Parameters," IEEE Transactions on Systems, Many and Cybernetics, 28(1):1-19 (Publication Date Unknown).

Watson et al., "Using Texture Maps to Correct for Optical Distortion in Head-Mounted Displays," Proceedings of the Virtual Reality Annual Symposium '95, IEEE, pp. 1-7 (1995).

Welch, Hybrid Self-Tracker: An Inertial/Optical Hybrid Three-Dimensional Tracking System, University of North Carolina Chapel Hill Department of Computer Science, TR 95-048.

William F. Garrett et al., "Real-Time Incremental Visualization of Dynamic Ultrasound Volumes Using Parallel BSP Trees, "Proceedings of IEEE Visualization 1996, pp. 235-240, available from www.cs.unc.edu/~andrei/pubs/1996_VIS_dualBSP_Mac.pdf, printed Sep. 20, 2007, 7 pages.

Yinghui et al., Real-Time Deformation Using Modal Analysis on Graphics Hardware, Graphite 2006, Kuala Lumpur, Malaysia, Nov. 29-Dec. 2, 2006.

Zitnick et al., "Multi-Base Stereo Using Surface Extraction," Visual Interface Inc., (Nov. 24, 1996).

U.S. Appl. No. 11/828,826, filed Jul. 26, 2007, Kurtis P. Keller et al.

Azuma et al., "Improving Static and Dynamic Registration in an Optical See-Through HMD," Paper Presented at SIGGRAPH '94 Annual Conference in Orlando, FL (1994).

Garrett, William F. et al., "Real-Time Incremental Visualization of Dynamic Ultrasound Volumes Using Parallel BSP Trees, "Proceedings of IEEE Visualization 1996, pp. 235-240, available from www.cs.unc.edu/~andrei/pubs/1996_VIS_dualBSP_Mac.pdf, printed Sep. 20, 2007, 7 pages.

InnerAim Brochure; 3D Visualization Software for Simpler, Safer, more Precise Aiming, Published no earlier than Apr. 1, 2010.

International Search Report and Written Opinion received in corresponding PCT Application No. PCT/US2010/024378, mailed Oct. 13, 2010, 9 pages.

InVision System Brochure; A "GPS" for Real-Time 3D Needle Visualization & Guidance, Published no. earlier than Mar. 1, 2008.

InVision User Manual; Professional Instructions for Use, Published no earlier than Dec. 1, 2008.

Jacobs, Marco C. et al., "Managing Latency in Complex Augmented Reality Systems," ACM SIGGRAPH Proceedings of the Symposium of Interactive 3D Graphics 1997, pp. 49-54, available from www.cs.unc.edu/~us/Latency//ManagingRelativeLatency.html, printed Sep. 20, 2007, 12 pages.

Livingston, Mark A. et al., "Magnetic Tracker Calibration for Improved Augmented Reality Registration," Presence: Teleoperators and Virtual Environments, 1997, vol. 6(5), pp. 532-546, available from www.cs.unc.edu/~andrei/pubs/1997_Presence_calibr.pdf, printed Sep. 20, 2007, 14 pages.

PCT, The Written Opinion of the International Searching Authority, mailed Mar. 3, 2011, for case PCT/US2010/043760.

Raij, A.B., et al., Comparing Interpersonal Interactions with a Virtual Human to Those with a Real Human; IEEE Transactions on Visualization and Computer Graphics 13(3), 443-457 (2007).

Raz et al, Real-Time Magnetic Resonance Imaging—Guided Focal Laser Therapy in Patients with Low-Risk Prostate Cancer, European Urology 58, pp. 173-177. Mar. 12, 2010.

Rosenthal, Michael et al., "Augmented Reality Guidance for Needle Biopsies: An Initial Randomized, Controlled Trial in Phantoms," Proceedings of Medical Image Analysis, Sep. 2002, vol. 6(3), pp. 313-320, available from www.cs.unc.edu/~fuchs/publications/.

* cited by examiner

SYSTEMS AND METHODS FOR DISPLAYING GUIDANCE DATA BASED ON UPDATED DEFORMABLE IMAGING DATA

CROSS-REFERENCE TO RELATED APPLICATION

This application claims the benefit of U.S. Provisional Application No. 61/068,469, filed Mar. 7, 2008.

BACKGROUND

Surgeons often need to be able to look at both pre-operative data, such as computed tomography ("CT") scans and magnetic resonance imaging ("MRI") scans, as well as intra operative data, such as two dimensional ("2D") ultrasound or three dimensional ("3D") ultrasound while they are in the operating room. Normally, doctors view the CT scans and ultrasound on separate displays and must use their imaginations in order to correlate the information in the two images. This is a difficult spatial task for the surgeons to accomplish. Further, when a target anatomical site is located within soft tissue, the pre-operative data is out of date with respect its pre-operative form because of the movement, compression and reorientation of the soft tissue and, therefore, it is difficult or impossible for the surgeon to appropriately utilize the pre-operative data during the operation.

Previous systems have attempted to aid the surgeon using computer vision registration techniques. Example systems are described in, among other papers, Aylward et al., *Analysis of the Parameter Space of a Metric for Registering* 3*D Vascular Images*, in W. Niessen and M. Viergever (Eds.), MEDICAL IMAGE COMPUTING AND COMPUTER-ASSISTED INTERVENTION—MICCAI 2001, pp. 932-939; and Aylward et al, *Intra-Operative* 3*D Ultrasound Augmentation*, Proceedings of the IEEE International Symposium on Biomedical Imaging, Washington, D.C., July 2002. The problem with these systems however is the massive computational strain required by the registration techniques.

SUMMARY

Presented herein are methods, systems, and computer-readable medium for presenting imaging data related to an anatomical site. These include obtaining a first set of imaging data related to the anatomical site and tracking units at the anatomical site and, thereafter, optionally, obtaining a second set of imaging data related to the anatomical site. A deformed version of the first set of imaging data is then determined based on the relative arrangements of one or more of the tracking units at the time when the first set of imaging data is obtained and when the second set of imaging data is obtained. Then the relative emplacements of the second set of imaging data and the deformed version of the first set of imaging data are determined and used, along with the second set of imaging data and the deformed version of the first set of imaging data, as a basis for displaying image guidance data.

Presented herein are methods, systems, and computer-readable medium for presenting imaging data related to an anatomical site, that include obtaining, at a first time, a first set of imaging data related to the anatomical site. Thereafter, tracking information for a movable imaging device controlled by a user is obtained at a second time, after the first time. Then desired emplacement information is determined for an image of the first set of imaging data based on the tracking information. Finally, image guidance data is determined for display based on the first set of imaging data and the desired emplacement information.

DETAILED DESCRIPTION OF SPECIFIC EMBODIMENTS

I. Overview

Figure 1:
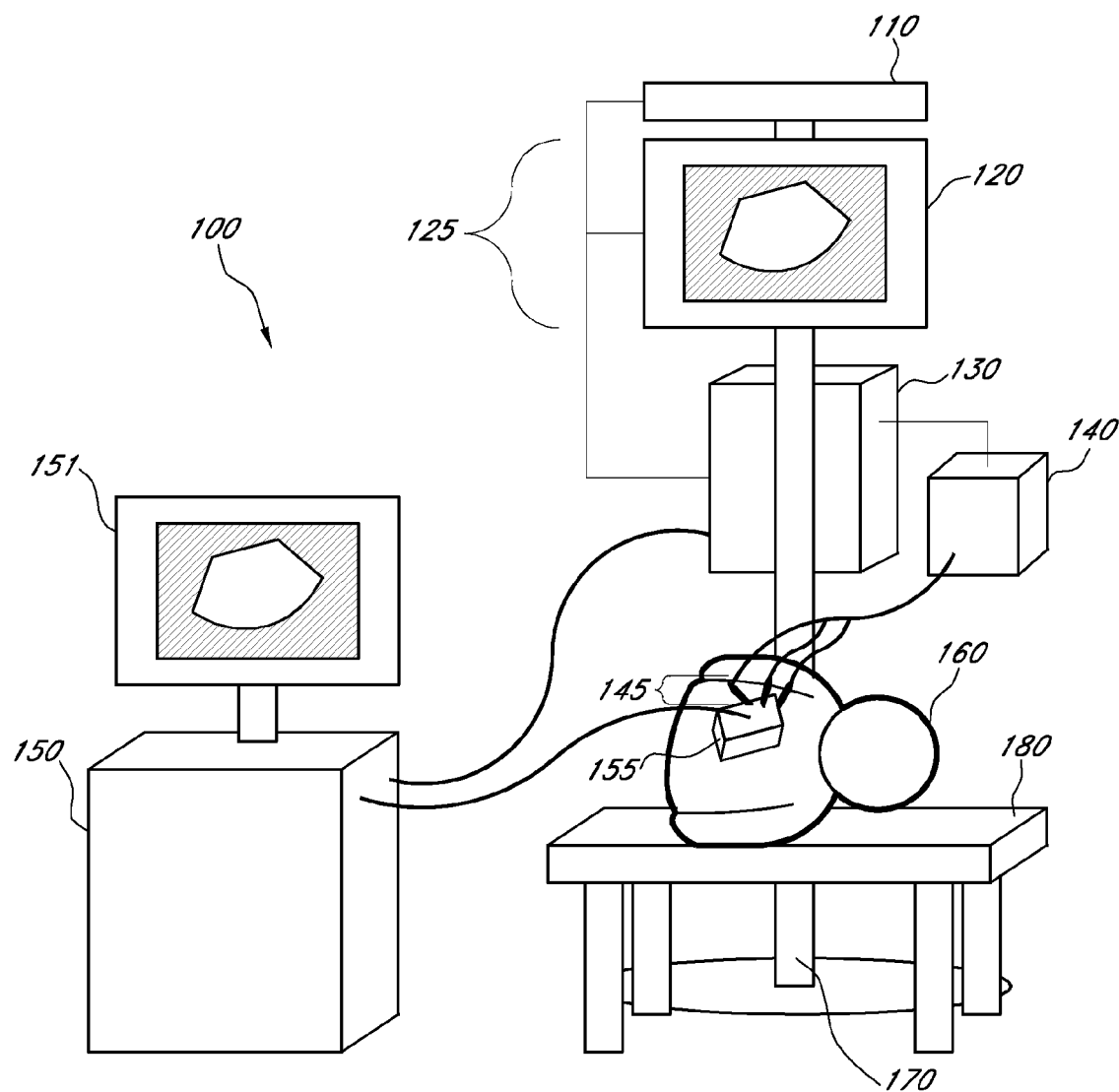
FIG. 1 depicts one embodiment of a system capable of updating deformable imaging data.

FIG. 1 depicts merely one exemplary embodiment of a system 100 capable of updating deformable imaging data. There are numerous other possible embodiments of system 100, for example, numerous of the depicted modules may be joined together to form a single module and may even be implemented in a single computer or machine. Further, the position sensing units 110 and 140 may be combined and track all relevant tracking units 145 and movable imaging units 155, as discussed in more detail below. Additionally, imaging unit 150 may be excluded and only imaging data from the image guidance unit 130 may be shown on display unit 120. These and other possible embodiments are discussed in more detail below. Numerous other embodiments will be apparent to those skilled in the art and are covered by the invention as claimed.

In the pictured embodiment, the system 100 comprises a first position sensing unit 110, a display unit 120, and the second position sensing unit 140 all coupled to an image guidance unit 130. In some embodiments, the first position sensing unit 110, the displaying unit 120, the second position sensing unit 140, and the image guidance unit 130 are all physically connected to stand 170. The image guidance unit 130 may be used to produce images 125 that are presented on display unit 120. As discussed more below, the images 125 shown on the display unit 120 by the image guidance unit 130 may be determined based on imaging data, such as a CT scan, MRI, open-magnet MRI, optical coherence tomography, positron emission tomography ("PET") scans, fluoroscopy, ultrasound, or other preoperative or intraoperative anatomical imaging data and any 3D anatomical imaging data. The images 125 produced may also be based on intraoperative or real-time data obtained using a movable imaging unit 155, which is coupled to imaging unit 150. Real-time may imply instantaneous or near-instantaneous obtaining of data. Real-time may also imply that it is taken with the intention to be used immediately. Imaging unit 150 may be coupled to image guidance unit 130. In some embodiments, imaging unit 150 may be coupled to a second display unit 151. The second display unit 151 may present imaging data from imaging unit 150. The imaging data displayed on display unit 120 and displayed on second display unit 151 are not necessarily the same. In some embodiments, the imaging unit 150 is an ultrasound machine 150, the movable imaging device 155 is an ultrasound transducer 155 or ultrasound probe 155, and the second display unit 151 is a display associated with the ultrasound machine 150 that shows the imaging data from the ultrasound machine.

The second position sensing unit 140 is coupled to one or more tracking units 145. The second position sensing unit 140 and tracking units 145 may together comprise a magnetic tracking system, an optical tracking system, or any other appropriate tracking system. The second position sensing unit 140 and tracking units 145 may be used to track the deformation of tissue at a target anatomical site on user 160. User 160 may be in an operating room, lying on an operating table, such as operating table 180, or in any other appropriate place or position. In various embodiments, second position sensing unit 140 may be an Ascension Flock of Birds, Nest of Birds, driveBAY, medSAFE, trakSTAR, miniBIRD, MotionSTAR, or pciBIRD, and tracking units 145 may be magnetic tracking coils. In some embodiments, the second position sensing unit 140 may be an Aurora® Electromagnetic Measurement System using sensor coils for tracking units 145. In some embodiments, the first position sensing unit 110 may also be an optical 3D tracking system using fiducials as tracking units 145. Such optical 3D tracking systems may include the NDI Polaris Spectra, Vicra, Certus, PhaseSpace IMPULSE, Vicon MX, InterSense IS-900, NaturalPoint OptiTrack, Polhemus FastTrak, IsoTrak, or Claron MicronTracker2.

Tracking unit 145 as used herein is a broad term and includes without limitation all types of magnetic coils or other magnetic field sensing devices for use with magnetic trackers, fiducials or other optically detectable markers for use with optical trackers, such as those discussed above and below. Tracking units 145 could also include optical position sensing devices such as the HiBall tracking system and the first and second position sensing units 110 and 140 may be HiBall tracking systems. Tracking units 145 may also include a GPS device or signal-emitting device that would allow for tracking of the position and, optionally, orientation of the tracking unit. In some embodiments, a signal-emitting device might include a radio-frequency identifier (RFID). In such embodiments, the first and/or second position sensing unit 110 and 140 may take in the GPS coordinates of the tracking units 145 or may, for example, triangulate the radio frequency signal being emitted by the RFID associated with tracking units 145.

Figure 8:
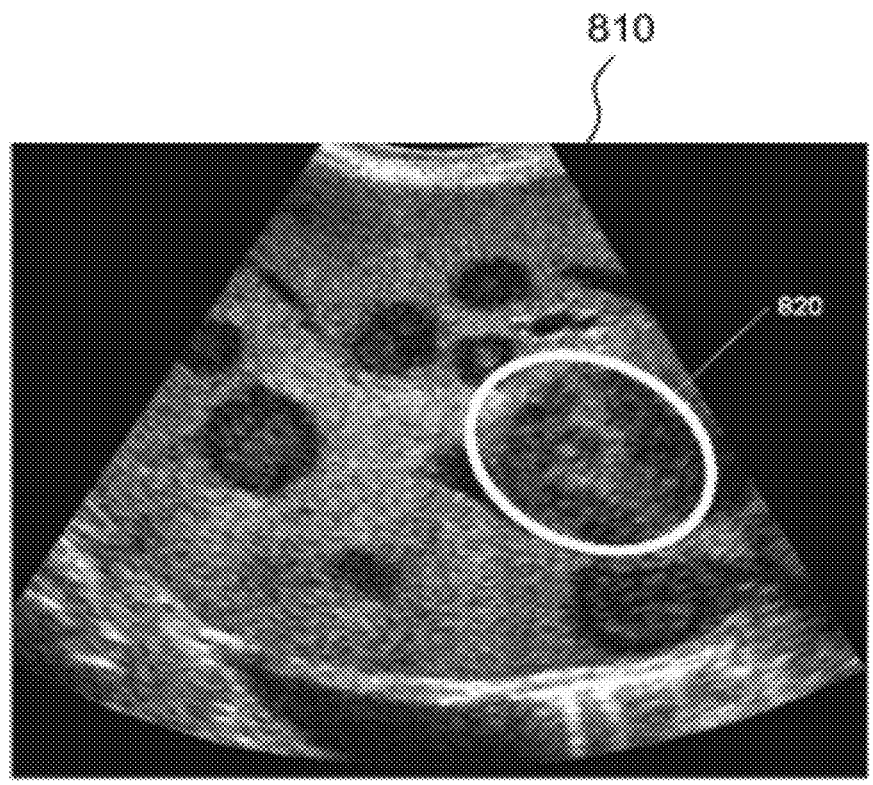
FIG. 8 depicts an embodiment of image guidance data in which first set of imaging data is presented with second set of imaging data.

The first position sensing unit 110 may be used to track the position of movable imaging unit 155. Tracking the position of movable imaging unit 155 allows for the determination of the relative emplacement, where emplacement may refer to position and orientation or merely position, of imaging data received using the movable imaging unit 155 and imaging unit 150 with that data being sent to image guidance unit 130. For example, image guidance unit 130 may contain CT data which is being updated and deformed based on the relative emplacements of tracking units 145 as received by the second position sensing unit 140. In such an example embodiment, the image guidance unit 130 may take in the emplacements, such as positions and orientations, of the tracking units 145 and from that determine an updated model for CT data stored in imaging guidance unit 130. Further, imaging guidance unit 130 may produce images based on the current ultrasound imaging data coming from imaging unit 150 and also based on an updated model determined based on the emplacements of tracking units 145. The images produced 125 made be presented on display unit 120. An example image 125 is shown in FIG. 8.

In some embodiments, a movable imaging unit 155 may not be connected directly to an imagining unit 150, but may instead be connected to imaging guidance unit 130. The movable imaging unit 155 may be useful for allowing a user to indicate what portions of a first set of imaging data should be displayed. For example, if the movable imaging unit 155 may be an ultrasound transducer or a tracked operative needle, for example, and may be used by a user to indicate what portions of a pre-operative CT scan to show on a display unit 120 as image 125. Further, in some embodiments, there could be a third set of pre-operative imaging data that could be displayed with the first set of imaging data. Yet further, in some embodiments, each of the first and third sets of imaging data could be deformed based on updated positions of the tracking units 145 and the updated, deformed versions of the two sets of imaging data could be shown together or otherwise provide image guidance images 125 for presentation on display 120.

First position sensing unit 110 may be an optical tracker, a magnetic tracker, or any other appropriate type of position sensing device. For example, in various embodiments, first position sensing unit 110 may be an Ascension Flock of Birds, Nest of Birds, driveBAY, medSAFE, trakSTAR, miniBIRD, MotionSTAR, or pciBIRD. In some embodiments, the first position sensing unit may be an Aurora® Electromagnetic Measurement System using sensor coils. In some embodiments, the first position sensing unit 110 may also be an optical 3D tracking system such as the NDI Polaris Spectra, Vicra, Certus, PhaseSpace IMPULSE, Vicon MX, InterSense IS-900, NaturalPoint OptiTrack, Polhemus FastTrak, IsoTrak, or Claron MicronTracker2. The first position sensing unit 110 senses the position of movable imaging unit 155. If first position sensing unit 110 is an optical tracker, then movable imaging unit 155 may have fiducials placed thereon to make visual position and/or orientation detection possible. If first position sensing unit 110 is a magnetic tracker, then movable imaging unit 155 they have placed thereon magnetic tracking units.

In some embodiments, the display unit 120 displays 3D images to a user. This can be accomplished by a stereoscopic display, a lenticular auto-stereoscopic display, or any other appropriate type of display. In some embodiments, a user may wear a head mounted display in order to receive 3D images from the image guidance unit 130. In such embodiments, a separate display, such as the pictured display unit 120, may be omitted.

In some undepicted embodiments, there is no first position sensing unit 110 and the emplacements of both the movable imaging unit 155 and tracking units 145 are determined using the second position sensing unit 140. Similarly, in some embodiments, the first position sensing unit 110 may track the emplacements of both the movable imaging unit 155 and tracking units 145 and the second position sensing unit 140 may not be present.

II. Anatomical Sites and Deformation

Figure 2:
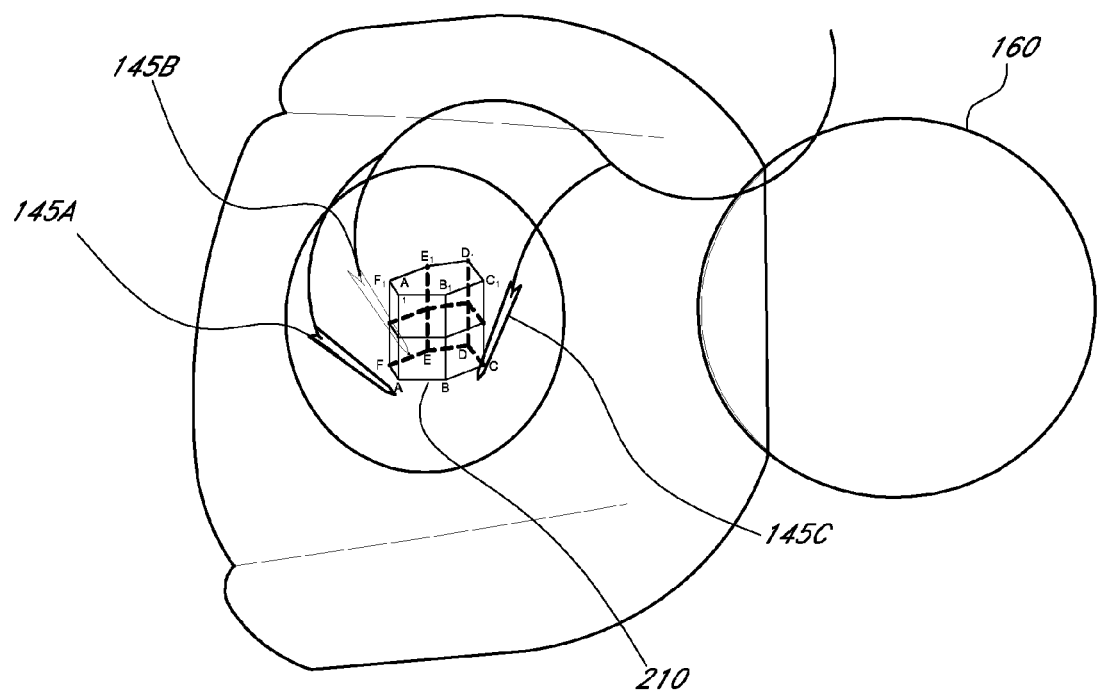
FIG. 2 illustrates an example of an anatomical site with tracking units.
Figure 4:
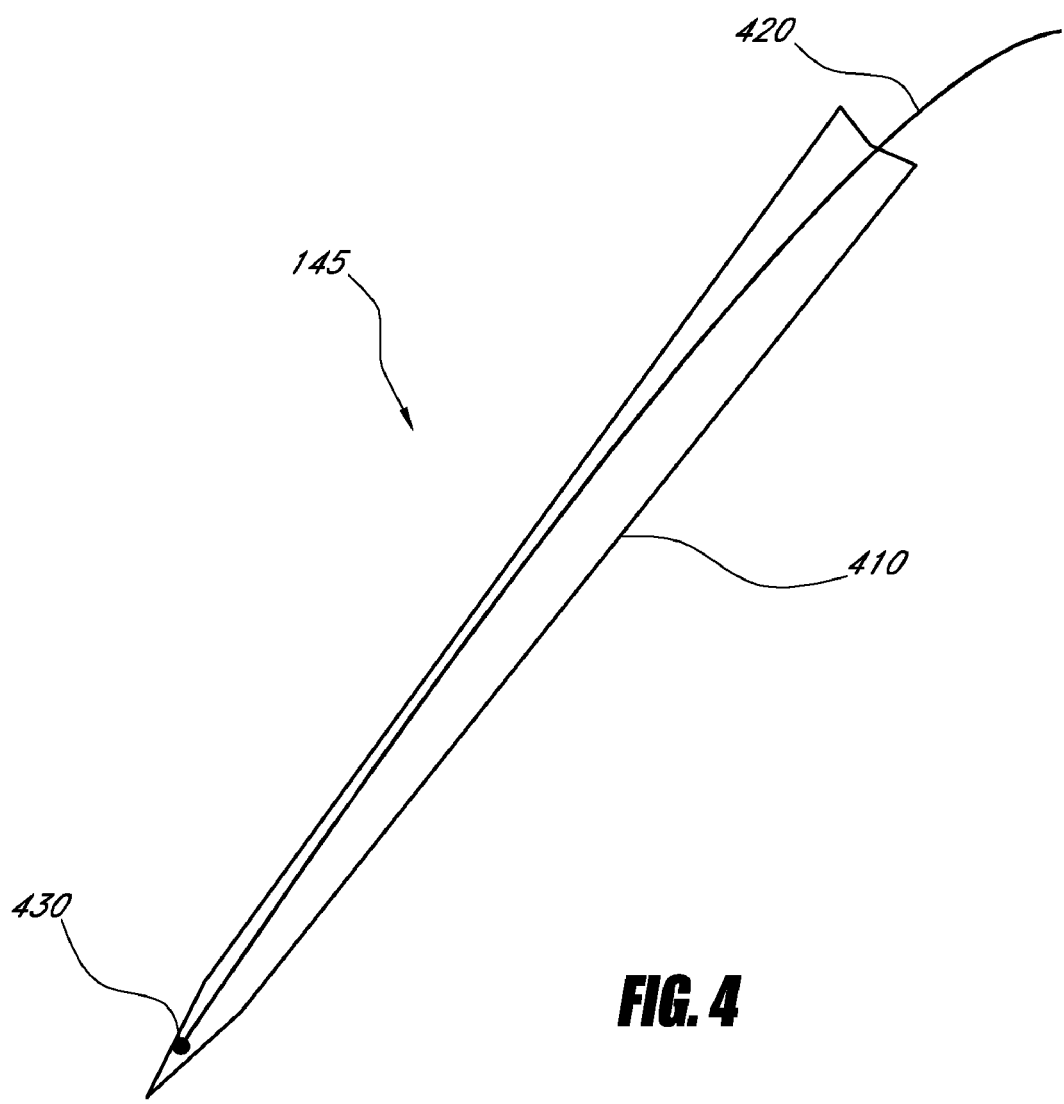
FIG. 4 depicts an embodiment of a tracking unit.

FIG. 2 illustrates an example of an anatomical site 210 with tracking units 145A, 145B, and 145C. An anatomical site 210 can be anywhere within or on the body 160, human or otherwise. In some embodiments, as shown in FIG. 4, tracking units 145A, 145B, and 145C may be implantable needles containing a magnetic tracking coil. If the tracking units 145A, 145B, and 145C are implantable, then the tracking units may be placed in or near an anatomical site 210. In some embodiments, tracking units 145A, 145B, and 145C may be placed on the surface of an anatomical site 210. In yet other embodiments, tracking units 145A, 145B, and 145C of known dimensions may be placed partially inside and partially external to an anatomical site 210. In such embodiments, a portion of the tracking unit 145A, 145B, and 145C may be in or near the anatomical site 210 while another portion may be external to the body or the anatomical site and allow tracking external to the body. This embodiment is useful, for example, if it is desired that the second position sensing unit 140 be an optical tracker or if there are other reasons, such as the size of a magnetic tracking coil, for not implanting that portion of the tracking units 145A, 145B, and 145C.

Figure 3:
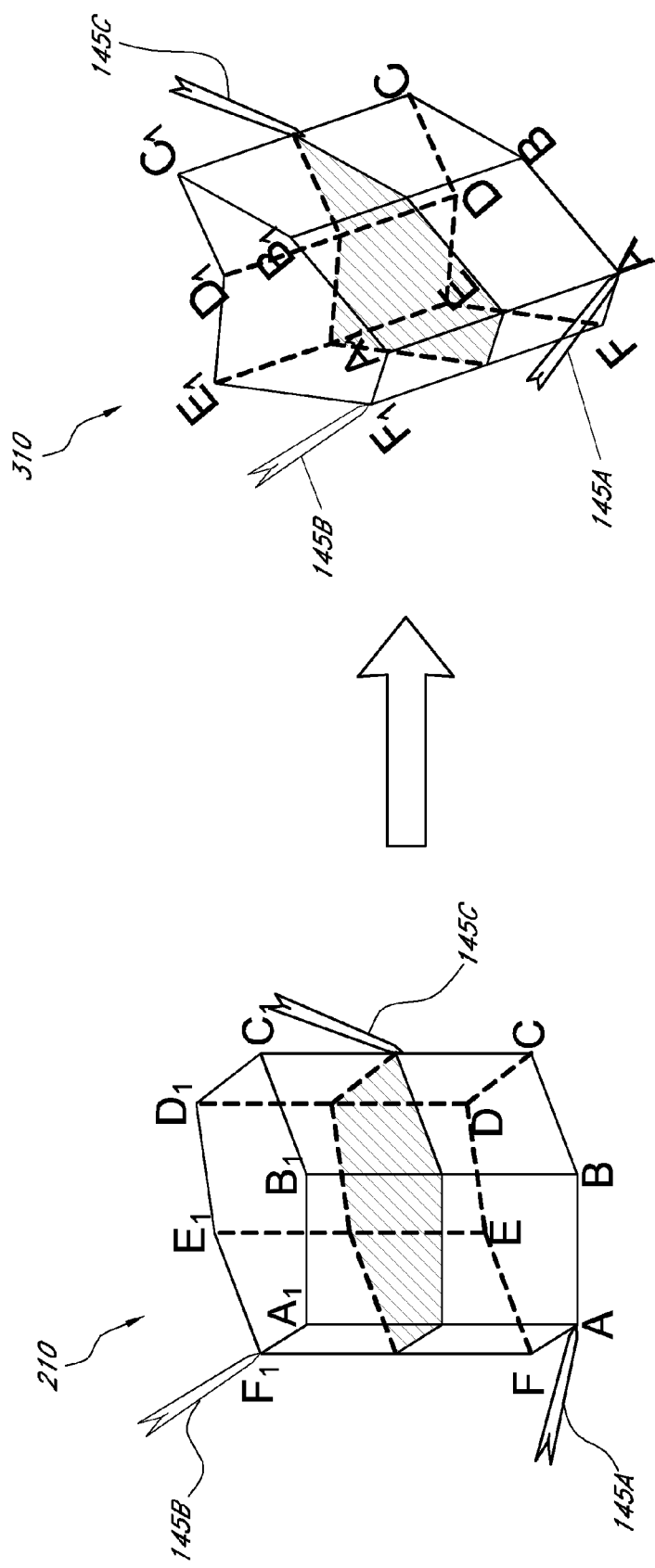
FIG. 3 illustrates the deformation of an anatomical site with tracking units.

FIG. 3 illustrates the deformation of an anatomical site 210 to 310 with tracking units 145A, 145B, and 145C. In FIG. 3, three tracking units 145A, 145B, and 145C have been placed near an anatomical site 210. The letters on the vertices of anatomical site 210 illustrate that anatomical site 210 may be deformed into deformed anatomical site 310. The letters illustrate which vertices in anatomical site 210 correspond to which vertices in deformed anatomical site 310. The deformation of anatomical site 210 into anatomical site 310 can be due to patient movement, breathing, pressure, force, or any other effect that may deform deformable tissue comprising and/or surrounding anatomical sites 210 and 310. FIG. 3 illustrates that the tracking units 145A, 145B, and 145C move from locations on anatomical sites 210 to corresponding locations in deformed anatomical site 310.

In some embodiments, the first set of imaging data, such as a CT scan, MRI, open-magnet MRI, fluoroscopy, PET scan, 3D ultrasound, or any other type of imaging data may be received in a format that is usable to perform the deformation techniques described herein. In other embodiments, when the first set of imaging data is received, a 3D model of that data may be produced. There are many known techniques for producing 3D models such as finite element models, volumetric models, or polygonal models. These include manual, human-driven techniques, such as tracing the boundaries of organs and tumors (also known as contouring), and automatic techniques such as iso-surface extraction (marching cubes, watershed), or hybrid techniques such as m-rep based segmentation. When the updated emplacement, such as position and orientation, or mere position, of the tracking units 145A, 145B, and 145C is determined, a model of the anatomical sites 210 can be updated to estimate the deformed anatomical site 310. This updating may be accomplished using known techniques for the various underlying models. For example, in some computer graphics hardware systems, one can use 3D textures. Each tracking unit can be associated with a texture location within the 3D texture, where the 3D texture comprises the first set of imaging data. Once updated positions of the tracking units 145A, 145B, and 145C are known, then the 3D texture can be updated using linear interpolation. Image guidance unit 130 may contain general hardware, such as a CPU, or specialized hardware, such as a graphics card, that is capable of performing linear interpolation on 3D textures. Relatedly, if a particular slice of the second set of imaging data is desired for display as part of image guidance data, then the particular slice for display may be determined based on the corresponding slice of the updated 3D texture. See, e.g., Yinghui, C., Jing, W., and Xiaohui, L. 2006, *Real-time deformation using modal analysis on graphics hardware*, in *Proceedings of the 4th international Conference on Computer Graphics and interactive Techniques in Australasia and Southeast Asia* (Kuala Lumpur, Malaysia, Nov. 29-Dec. 2, 2006). GRAPHITE '06. ACM, New York, N.Y., 173-176. Another example embodiment of linear deformation is discussed below. Other embodiments, bi-cubic or higher-order interpolation may also be used. Additionally, in some embodiments, the tracking units 145A, 145B, and 145C provide position data and not orientation data. Deformation of the 3D model can be accomplished based on the position of the tracking units 145A, 145B, and 145C. In some embodiments, the tracking units 145A, 145B, and 145C will provide both position and orientation data. The additional information on orientation can be used to provide a different kind of deformation of the model.

In some embodiments, once a new 3D model for deformed anatomical site 310 is determined, the updated model can be used, for example, by image guidance unit 130 of FIG. 1 in order to produce image guidance data that is based on a combination of imaging data from imaging unit 150 and movable imaging unit 155. This image guidance data may be displayed as imaging data 125 on display unit 120.

FIG. 4 depicts an embodiment of a tracking unit 145. In some embodiments, the tracking unit 145 comprises a shaft 410, a magnetic coil 430, and a cable 420. The shaft 410 may be a hollow needle or any implantable unit. The shaft 410 may be hollow in order to accommodate insertion of the cable 420 and magnetic coil 430, or may be solid, in which case magnetic coil 430 and cable 420 must be built into the shaft 410 or the shaft 410 must be constructed around the magnetic coil 430 and cable 420. As noted above, in some embodiments a tracking unit 145 may include an optical device, such as a fiducial (not pictured), in order to allow proper tracking. In yet other embodiments, a tracking unit 145 may include an implantable portion in addition to and separate from the tracking portion (not pictured).

Figure 5:
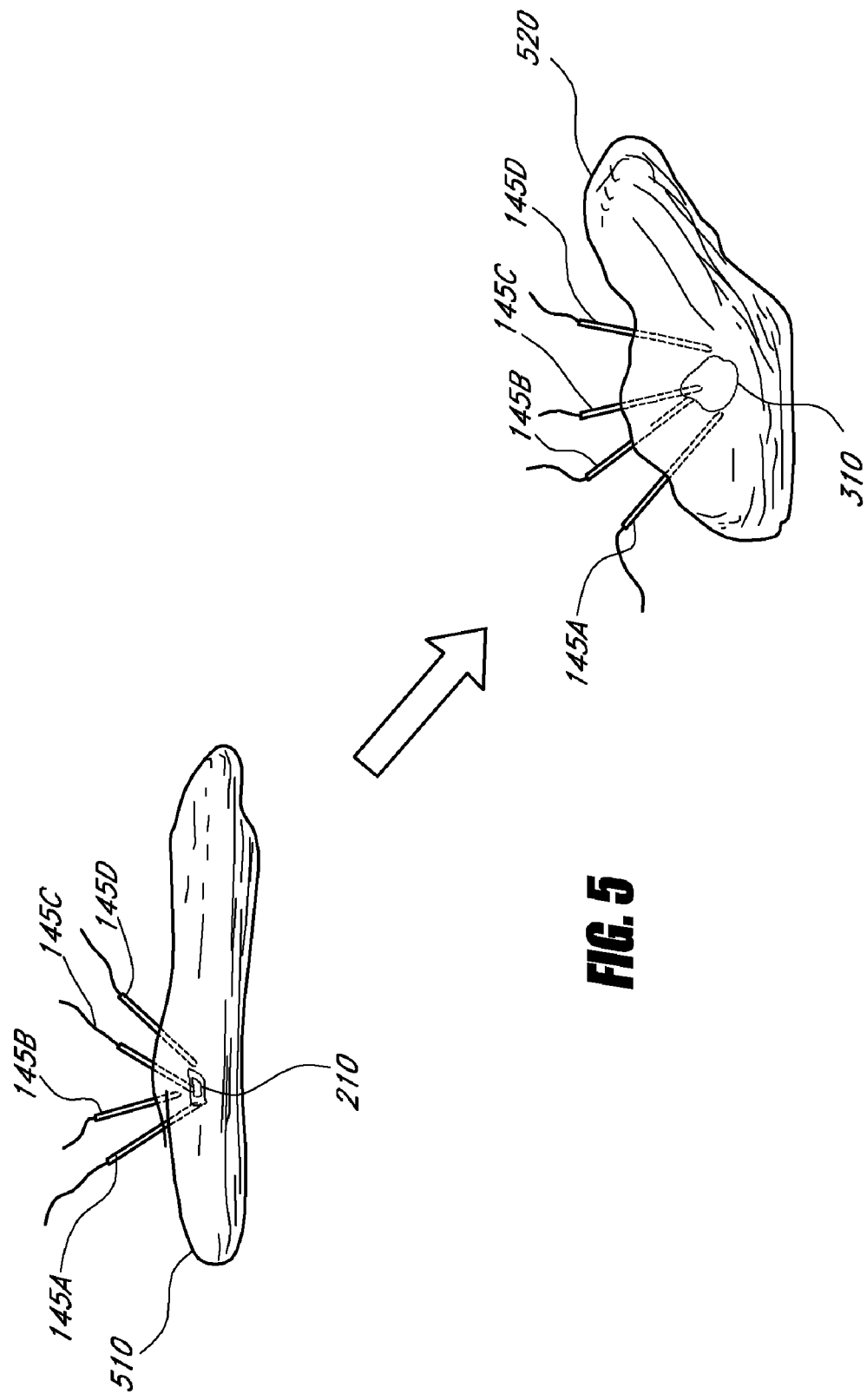
FIG. 5 illustrates another example of an anatomical site within deformable tissue with tracking units.

FIG. 5 illustrates another example of an anatomical site 210 within deformable tissue 510 with implanted tracking units 145A, 145B, 145C, and 145D. FIG. 5 illustrates that the deformable tissue 510 deforms into deformable tissue 520. Similar to the embodiments shown in FIG. 3, anatomical site 210 is deformed into deformed anatomical site 310. Tracking units 145A, 145B, 145C, and 145D are shown implanted near anatomical site 210. The tracking units 145A, 145B, 145C, and 145D remain near the anatomical site after deformable tissue 510 has been deformed into deformed deformable tissue 520, and anatomical site 210 has deformed into deformed anatomical site 310. As was the case in the embodiment shown in FIG. 3, a 3D model of anatomical site 210 can be deformed and updated based on the relative emplacements of the tracking units 145A, 145B, 145C, and 145D at the time before and after deformation.

III. Process for Providing Guidance Data

Figure 6:
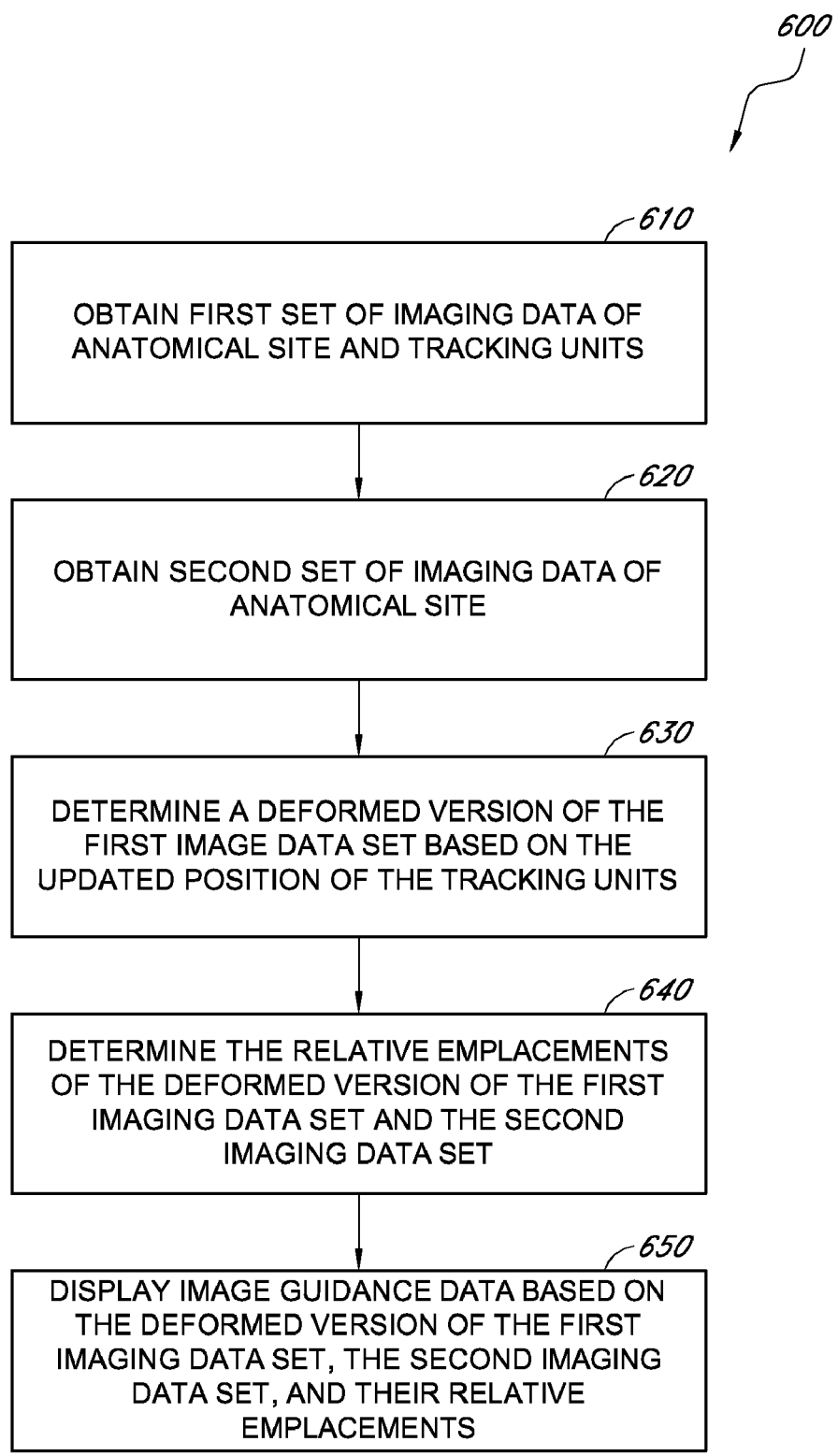
FIG. 6 depicts an example process for providing guidance data based on updated deformable tracking information.

FIG. 6 depicts one of many possible example processes 600 for providing guidance data based on updated deformable tracking information. In some embodiments, all or portions of process 600 may be performed by image guidance system 130 or by any other appropriate unit or module. In step 610, a first set of imaging data from anatomical site 210 and tracking units 145 is obtained. This first set of imaging data may be a CT scan, MRI, open-magnet MRI, fluoroscopy, PET scan, 3D ultrasound, or any other imaging data. Obtaining the relative emplacements of the tracking units 145 when taking the data for the anatomical site 210 provides the ability to determine how the relative emplacements of the tracking units 145 have changed, from the time that the first set of imaging data is taken, and until any time later at which the emplacements of the tracking units are known. Generally, the tracking units 145 will be visible in the first set of imaging data, but this is not necessary. The tracking units 145 must simply be close enough to an anatomical site of interest to provide information on deformation of the anatomical site.

In some embodiments, once a first set of imaging data of the anatomical site and tracking units 145 is obtained, a 3D model of the first set of imaging data is produced. In other embodiments, a 3D model of the first set of imaging data is produced at a later time or is not produced at all, and deformation of the first set of imaging data is accomplished without using a 3D model. The production of a 3D model from the first set of imaging data is discussed above.

At some time after the first of imaging data is obtained in step 610, a second set of imaging data of the anatomical site is obtained in step 620. The second set of imaging data may, like the first set of imaging data, be any of a variety of types of imaging data. For example, a second set of imaging data may be 2D ultrasound, 3D ultrasound, fluoroscopy, or any other type of imaging data. The tracking units 145 may, but need not, be visible in the second set of imaging data. For example, if the second set of imaging data is 2D ultrasound, then the ultrasound image obtained may include a plane or slice of the anatomical site 210, but tracking units 145 need not be visible in that particular slice or plane.

In step 630, a deformed version of the first set of imaging data is determined. In some embodiments, updated emplacements of the tracking units 145, at the time the second set of imaging data is obtained, are used to determine an updated or deformed model of the first set of imaging data. This is discussed above. Once the updated or deformed version of the first set of imaging data and the recently obtained second set of imaging data are both available, the relative emplacements of those two sets of imaging data are determined. This may be accomplished based on both the emplacements of the tracking units 145, in order to determine the emplacement of the deformed version of the first set of imaging data, and the emplacement of the second set of imaging data. The emplacements of the second set of imaging data may be determined based on, for example, the location of a movable imaging unit 155, as depicted in FIG. 1. As another example embodiment, if a movable imaging unit 155 is a 2D ultrasound wand, then tracking the location of a movable imaging unit 155 allows determination of the position and orientation of the second set of imaging data. As noted above, the movable imaging unit 155 may be tracked using the first position sensing unit 110. In some embodiments, the determination of relative emplacements of the two imaging data sets may take the form of a 3D transformation or other mathematical relationship.

Once the relative positions of the second set of imaging data and the deformed version of the first set of imaging data are known, the image guidance data can be determined and displayed in step 650. In some embodiments, the image guidance data shows features within the deformed version of the first set of imaging data in combination with a second set of imaging data, such as that depicted in FIG. 8. In other embodiments, the image guidance data may be an overlay or a combination of the second set of imaging data and of the deformed version of the first set of imaging data. Other examples of image guidance data that may be displayed in step 650 are those depicted in FIGS. 7A-7D, discussed below.

In some embodiments, each time that more imaging data is received from the data source that provided the second set of imaging data, process 600 may repeat starting at step 620. Process 600 may also be restarted from step 610, especially in scenarios, such as resection at the anatomical site, where warping of the first set of imaging data is no longer possible. In such a case, the first set of imaging data may be re-obtained in step 610.

As noted above, in some embodiments, the deformation is accomplished by linear deformation. Linear deformation may be accomplished in number of ways, including using graphics hardware. As one example embodiment of linear deformation, consider an original volume image I (as scanned, for example, by the CT scanner at time t) as an anatomical site of interest. At time t, there are n tracking units implanted in the tissue near and around the anatomical site. The tracking units' positions are $pt_1 \ldots pt_n$. For each tracking unit, we compute the 3d texture coordinate, tc, that indicates the position of the tracking sensor, in image I's coordinate system. 3d texture coordinates may lie in the range $u=[0 \ldots 1]$, $v=[0 \ldots 1]$, $w=[0 \ldots 1]$. The eight corners of the image I in the 3d texture's coordinate system may be (0,0,0), (0,0,1), (0,1,0), (0,1,1), (1,1,0), (1,1,1). The points may then be stored in a table-like data structure as follows:

| Points table: |
| --- |
| point #1, $pt_1.x$, $pt_1.y$, $pt_1.z$, $tc_1.u$, $tc_1.v$, $tc_1.w$, |
| point #2, $pt_2.x$, $pt_2.y$, $pt_2.z$, $tc_2.u$, $tc_2.v$, $tc_2.w$, |
| point #3, $pt_3.x$, $pt_3.y$, $pt_3.z$, $tc_3.u$, $tc_3.v$, $tc_3.w$, |
| ... |
| point #n, $pt_n.x$, $pt_n.y$, $pt_n.z$, $tc_n.u$, $tc_n.v$, $tc_n.w$, | where $pt_k.y$ and $tc_k.u$ refer, for example, to point $pt_k$'s y coordinate and $tc_k$'s u coordinate, respectively.

The volume may then be tessellated into tetrahedra. The corner point of each tetrahedron k may be one of n tracking units, at position $pt_k$. The edges of the tessellation may be stored in a data structure as follows:

| Edges table: |
| --- |
| edge #1, point $a_1$, point $b_1$, |
| edge #2, point $a_2$, point $b_2$, |
| ... |
| edge #m, point $a_n$, point $b_n$, | where each edge connects two points, each of which is a reference to a point #. For example, point $a_1$ may refer to point #1 and point $b_1$ may refer to point #4.

| Tetrahedra table: |
| --- |
| tetrahedron #1, edge $a_1$, edge $b_1$, edge $c_1$, edge $d_1$, edge $e_1$, edge $f_1$, |
| tetrahedron #2, edge $a_2$, edge $b_2$, edge $c_2$, edge $d_2$, edge $e_2$, edge $f_2$, |
| ..., | where edge $a_1$ and $a_2$ may refer, for example, to edges #5 and edge #2, respectively.

Some of the image I may lie outside of the convex hull of the points $pt_1 \ldots pt_n$. These portions of image I may be ignored or other algorithms may be used to determine their distortion.

At time j, where j>t, the tissue may have changed shape, and image I (which represents the anatomical site at time t) may no longer represent the. The positions of the tracking sensors at time j, are $pj_1 \ldots pj_n$. One may consider a new image J that is a linearly warped copy of image I. One may not need to compute image J, however. Instead, at time j, an updated, deformed image for a 2d cross-sectional plane through image J may be determined as follows:

Update the points table, and replace each $pt_k$ with $pj_k$ where $k=\{1 \ldots n\}$, thereby updating the position of each tracking unit, at time j, as supplied, for example, by position sensing system 140.

Iterate through the tetrahedra table. For each tetrahedron, iterate through each of its six edges. For each such edge, compute its intersection with the cross-sectional plane. For those edges that do intersect with the plane, we compute the intersection point P. We then compute the texture coordinate for P, by linearly interpolating between the texture coordinates at its endpoints (those texture coordinates are stored in the points table).

For each tetrahedron, there will be 0, 1, 2, 3, or 4 edges that intersect with the plane (resulting in 0, 1, 2, 3, or 4 intersections points P, and their corresponding texture coordinates).

When there are 0, 1, or 2 intersections, render nothing associated with the tetrahedron.

When there are 3 or 4 intersections of the cross-sectional plane, render a textured polygon using traditional graphics hardware commands (e.g. OpenGL or DirectX). The texture coordinates index into the image I, but because the point P will have moved from the original location, the result will be a portion of image J.

Repeat this for each tetrahedron. After all tetrahedra have been processed, the graphics hardware will have rendered the intersection of the warped image J, with the chosen cross-sectional plane.

In some embodiments, if the second set of imaging data is a planar fluoroscopic image, then the deformed version of the first set of imaging data may be projected onto the plane of the planar fluoroscopy and the two images may be combined in order to produce the image guidance data.

In some embodiments, the image guidance data determined in step 650 from the deformed version of the first set of imaging data could be used to approximate another imaging modality. For example, the first set of imaging data may be a CT scan and a user may wish to have an approximation of a biplane fluoroscopy performed without exposing a patient to the harmful radiation associated with such a fluoroscopy. The deformed version of the first set of imaging data may be projected onto what would be the two planes of the biplane fluoroscopy. This would approximate the biplane fluoroscopy using the updated tracking unit information without exposing the patient to the radiation associated with the biplane fluoroscopy. Further, this approximation could be updated at a rate that exceeds that of conventional biplane fluoroscopy as the tracking units move with the surrounding tissues to which they are affixed, without harming the patient or disturbing the ongoing operation.

IV. Creating Features in Imaging Data

Figure 7A:
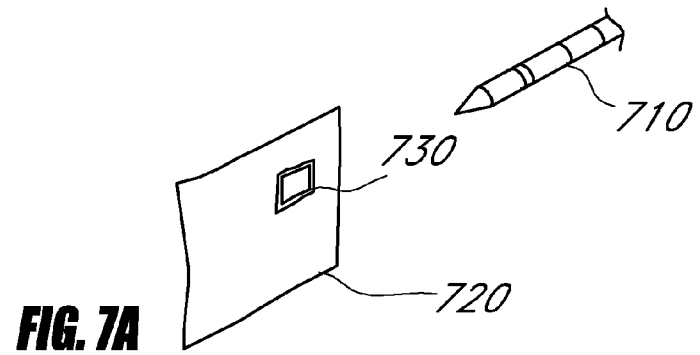
FIGS. 7A-7D depict marking and viewing features in imaging data.
Figure 7B:
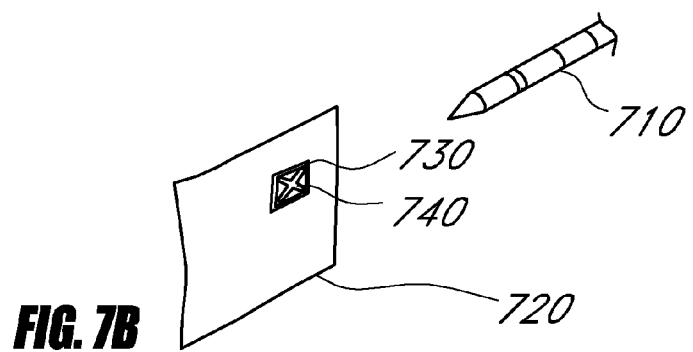
Figure 7C:
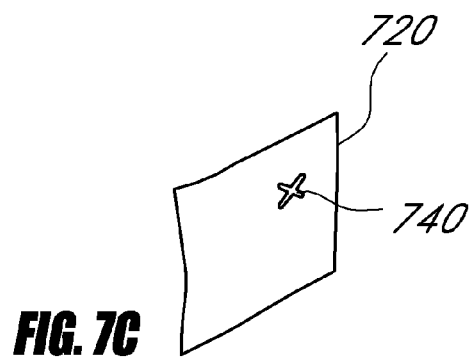

FIGS. 7A-7D depict marking and viewing features in imaging data. Generally FIGS. 7A-7D show the manual creation of features within a first set of imaging data and updating the placement of the feature based on the deformed model of the first set of imaging data. FIG. 7A shows a feature selection unit 710 being used to highlight, in a particular plane or visual slice of the first set of imaging data 720, a feature 730 within the first of imaging data. In FIG. 7B, the user points to the feature 730 and selects the feature in order to signify selected feature 740. When the first set of imaging data 720 is being viewed later, the selected feature 740 will still appear in its original position, as depicted in FIG. 7C.

Figure 7D:
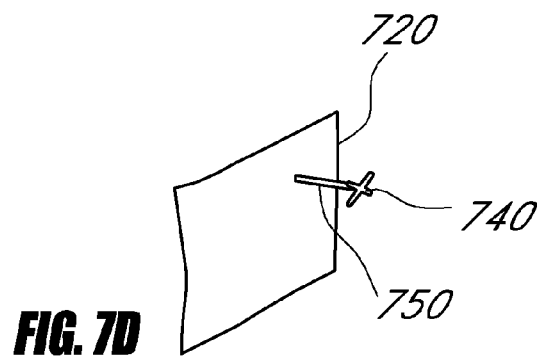

FIG. 7D illustrates that if a plane of the first set of imaging data 720 is displayed, and the selected feature 740 may still be displayed even if it is not within the visual slice or plane or display data of the first set of imaging data 720. The displacement of the feature 740 from the visual slice of the first set of imaging data 720 may be shown with a displacement marker 750. In some embodiments, the displacement of the selected feature 740 from the visual slice of the first set of imaging data 720 may be shown with other visual techniques, such as visual depth on a 3D display, shadowing, foreshortening, or any other known technique. In FIGS. 7C and 7D, even if the first set of imaging data is deformed based on updated emplacements of the tracking units 145 (not pictured), the selected feature 740 may be shown in a new location based on the deformation of the first set of imaging data 720. Marking these features may be useful so that a user or surgeon could identify and later find points of interest, such as locations of tumors or lesions.

V. Image Guidance Data

FIG. 8 depicts an embodiment of image guidance data in which a first set of imaging data is presented with a second set of imaging data. In some embodiments, the second set of imaging data is displayed in approximately the form that is received as described above. The first of imaging data may be deformed based on the updated emplacements of tracking units 145. The updated or deformed model corresponding to the first set of imaging data may be used to provide image guidance, such as the location of an important feature of the anatomical site. For example, in the ultrasound image of the liver depicted in FIG. 8, the ultrasound image 810 (the second set of imaging data) is augmented with a feature 820 from the first set of imaging data, such as a CT scan. This feature may be the location of a tumor, necrosed tissue, or any other relevant feature. It may have been detected or selected by a user, as illustrated in FIGS. 7A-7D. Upon deformation of the underlying tissue, the model for the first set of imaging data may be deformed and therefore the feature 820 shown from the second set of imaging data would also be updated and deformed. Over time, as new second sets of imaging data 810 were being generated, the movement and updated emplacements of the tracking units 145 in an anatomical site would cause the deformation and movement of the feature of the first set of imaging data 820. The updated emplacement of the feature 820 would continue to be shown with the newly received second set of imaging data 810. In some embodiments, the deformation of the first set of imaging data approximates the deformation of the underlying tissue. Therefore, the approximate placement of the feature 820 would approximate the location of the underlying anatomical feature within the second set of imaging data 810.

The processes, computer readable medium, and systems described herein may be performed on various types of hardware, such as computer systems. Computer systems may include a bus or other communication mechanism for communicating information, and a processor coupled with the bus for processing information. A computer system may have a main memory, such as a random access memory or other dynamic storage device, coupled to the bus. The main memory may be used to store instructions and temporary variables. The computer system may also include a read-only memory or other static storage device coupled to the bus for storing static information and instructions. The computer system may also be coupled to a display, such as a CRT or LCD monitor. Input devices may also be coupled to the computer system. These input devices may include a mouse, a trackball, or cursor direction keys. Computer systems described herein may include the image guidance unit 130, first and second position sensing units 110 and 140, and imaging unit 150. Each computer system may be implemented using one or more physical computers or computer systems or portions thereof. The instructions executed by the computer system may also be read in from a computer-readable medium. The computer-readable medium may be a CD, DVD, optical or magnetic disk, laser disc, carrier wave, or any other medium that is readable by the computer system. In some embodiments, hardwired circuitry may be used in place of or in combination with software instructions executed by the processor.

As will be apparent, the features and attributes of the specific embodiments disclosed above may be combined in different ways to form additional embodiments, all of which fall within the scope of the present disclosure.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

Any process descriptions, elements, or blocks in the flow diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

All of the methods and processes described above may be embodied in, and fully automated via, software code modules executed by one or more general purpose computers or processors, such as those computer systems described above. The code modules may be stored in any type of computer-readable medium or other computer storage device. Some or all of the methods may alternatively be embodied in specialized computer hardware.

It should be emphasized that many variations and modifications may be made to the above-described embodiments, the elements of which are to be understood as being among other acceptable examples. All such modifications and variations are intended to be included herein within the scope of this disclosure and protected by the following claims.

What is claimed is:

1. A method of presenting imaging data related to an anatomical site, comprising:
    obtaining a first set of imaging data related to an anatomical site at a first time;
    obtaining information on one or more tracking units at the anatomical site at the first time;
    obtaining tracking information for a movable imaging device controlled by a user at a second time, after the first time;
    obtaining information on the one or more tracking units at the anatomical site at the second time;
    determining desired emplacement information for an image of the first set of imaging data based on the tracking information;
    determining a deformed version of the first set of imaging data based on a first location of the one or more tracking units at the first time and a second location of the one or more tracking units at the second time that is different from the first location; and
    determining image guidance data for display based on the first set of imaging data, the deformed version of the first set of imaging data and the desired emplacement information.

2. The method of claim 1, wherein the method further comprises:
    obtaining at a third time, before the second time, a second set of imaging data; and
    wherein:
    determining image guidance data for display comprises determining image guidance data for display based on the first set of imaging data, the deformed version of the first set of imaging the second set of imaging data, and the desired emplacement information.

3. The method of claim 1, wherein determining image guidance data for display comprises approximating a bi-plane fluoroscopy.

4. The method of claim 1, wherein obtaining a first set of imaging data related to the anatomical site comprises obtaining an arrangement of tracking units at the anatomical site.

5. The method of claim 1, further comprising receiving information about a feature within the first set of imaging data, wherein determining image guidance data for display comprises displaying the feature within the first data set.

6. The method of claim 1, wherein the movable imaging device is a movable ultrasound device.

7. The method of claim 1, wherein determining a deformed version of the first set of imaging data comprises performing a linear interpolation on a model of the first set of imaging data.

8. The method of claim 1, wherein determining a deformed version of the first set of imaging data comprises performing a bi-cubic interpolation on a model of the first set of imaging data.

9. The method of claim 1, wherein determining the deformed version of the first set of imaging data comprises performing a deformation on a volumetric model of the first set of imaging data based on the arrangements of the tracking units at the first time and at the second time.

10. The method of claim 2, wherein the second set of imaging data is associated with the movable imaging device and the emplacement of the second set of imaging data is determined using the emplacement of the movable imaging device.

11. The method of claim 2, wherein the second set of imaging data is associated with movable imaging device and the emplacement of the second set of imaging data is determined using the emplacement of a second movable device, wherein the movable imaging device is distinct from the second movable device.

12. The method of claim 4, wherein obtaining an arrangement of the tracking units comprises determining the location and orientation of the tracking units.

13. The method of claim 4, wherein obtaining the first set of imaging data comprises obtaining a volumetric model of obtained imaging data including the emplacement of the tracking units, wherein the method further comprises determining a deformed version of the first set of imaging data by performing a deformation of the volumetric model.

14. The method of claim 4, wherein automatically obtaining the first set of imaging data comprises obtaining a finite element model of obtained imaging data including the emplacement of the tracking units; wherein the method further comprises determining a deformed version of the first set of imaging data by performing a deformation of the finite element model.

15. The method of claim 11, wherein the movable imaging device is a movable 3D ultrasound device and the second movable device is a display indication device.

16. A system for presenting imaging data related to an anatomical site, comprising:
- an image guidance system in communication with one or more tracking units at an anatomical site, the image guidance system configured to:
  - obtain a first set of imaging data related to the anatomical site at a first time;
  - obtain location information of the one or more tracking units at the first time;
  - obtain tracking information for a movable imaging device controlled by a user at a second time, after the first time;
  - obtain location information of the one or more tracking units at the second time;
  - determine desired emplacement information for an image of the first set of imaging data based on the tracking information; and
  - determine a deformed version of the first set of imaging data based on a first location of the one or more tracking units at the first time and a second location of the one or more tracking units at the second time that is different from the first location; and
  - determine image guidance data for display based on the first set of imaging data, the deformed version of the first set of the first set of imaging data, and the desired emplacement information.

17. A computer-readable medium that executes the steps for presenting imaging data related to an anatomical site, comprising:
- obtaining a first set of imaging data related to an anatomical site at a first time;
- obtaining information on tracking units at the anatomical site at the first;
- obtaining tracking information for a movable imaging device controlled by a user at a second time, after the first time;
- obtaining information on the tracking units at the anatomical site at the second time; determining desired emplacement information for an image of the first set of imaging data based on the tracking information;
- determining a deformed version of the first set of imaging data based on a first location of the tracking units at the first time and a second location of the tracking units at the second time that is different from the first location; and
- determining image guidance data for display based on the first set of imaging data, the deformed version of the first set of imaging data, and the desired emplacement information.

* * * * *